United States Patent [19]

Roeder

[11] Patent Number: 4,505,704
[45] Date of Patent: Mar. 19, 1985

[54] SANITARY NAPKIN WITH MULTI-CONFIGURATIONAL CAPABILITIES

[75] Inventor: Robert J. Roeder, Outagamie County, Wis.

[73] Assignee: Kimberly-Clark Corporation, Neenah, Wis.

[21] Appl. No.: 403,991

[22] Filed: Aug. 2, 1982

[51] Int. Cl.³ .............................................. A61F 13/16
[52] U.S. Cl. .................................... 604/385; 128/170
[58] Field of Search .............. 604/364, 365, 385, 358; 128/155, 156, 170

[56] References Cited

U.S. PATENT DOCUMENTS

| | | | |
|---|---|---|---|
| 2,476,869 | 7/1949 | Hughes | 604/385 |
| 2,771,882 | 11/1956 | Leupold | 604/385 |
| 3,336,923 | 8/1967 | Devaud | 128/156 |
| 3,758,363 | 9/1973 | Frick | 604/358 X |
| 4,347,092 | 8/1982 | Hlaban et al. | 604/365 |

FOREIGN PATENT DOCUMENTS 360020 12/1905 France .................................. 128/170

*Primary Examiner*—John D. Yasko
*Attorney, Agent, or Firm*—Howard Olevsky; R. Jonathan Peters

[57] ABSTRACT

A sanitary napkin is provided in elongate sheet form such that the fluid impervious baffle, the absorbent, and the fluid impervious cover are coterminous at the longitudinal edges and the napkin stock itself extends at least about four times the length of a conventional mini pad. This sheet stock can be shaped by the ultimate user not only longitudinally to provide the precise length, but also in any configuration desired.

In another form the invention contemplates this napkin sheet stock in roll form packaged in a dispenser which preferentially has means for longitudinal cutting.

6 Claims, 2 Drawing Figures

SANITARY NAPKIN WITH MULTI-CONFIGURATIONAL CAPABILITIES

FIELD OF THE INVENTION

This invention relates to hygenic appliances, and particularly sanitary napkins.

BACKGROUND OF THE INVENTION

Sanitary napkins generally fall into three basic categories which relate generally to napkin size. The largest of the types of napkins is the maxi pad. This napkin which is hypothetically at least designed for maximum absorbency is relatively longer than the other types of napkins and generally has more absorbent and is of a higher bulk. Maxi pads are generally characterized by parallel edges on the longitudinal axis and the width of the maxi pad varies generally between about two and three inches.

On the other extreme is the so called pantiliner product which is extremely thin and four or five inches in length and designed to offer protection only for light discharge. The mini pad is the third type which is more nearly similar to the maxi pad in that it is substantially thicker and longer than the pantiliner type of product but is still less thick and not as long as the maxi pad.

It will be noted from the above discussion that the napkins are designed primarily in response to perceived concepts of absorbency needs, but are not really designed to take into account the individual variances in shape in the perineal area of the wearer. As evidence of this, napkins after use tend to be folded and distorted and the distortion patterns may actually be different from wearer to wearer. Also, many napkins fail because of the non-planar distortion accompanying the forces placed on the napkin surface due to normal movements.

The napkin made according to the teachings of this invention has the geometry shaped by the user according her perceived needs and desires.

SUMMARY OF THE INVENTION

According to this invention, a continuous strip of napkin material having a fluid pervious cover, an absorbent layer and a fluid impermeable baffle is provided. This strip is coterminous along the longitudinal edges and may extend to the length of at least 24 inches or more.

In a particularly preferred embodiment, this strip is configured in a single width roll. This roll can be mounted for rotation and unwound as needed. In a particularly preferred embodiment the roll is designed for mounting in a dispenser which may be provided with a cutting edge to allow for a transverse tear to separate a segment of the length desired by the user. This dispenser may be either decorative and capable of accepting refills or the roll may be packaged in a suitable sales container having a suitable dispenser. After the length of the segment is determined, either by means of a cutting edge on the dispenser or by any other conventional cutting action, the napkin can be preshaped by the same cutting mechanism to provide a configuration which is more comfortable than the shape of the conventional napkin to the particular user.

U.S. Pat. No. 3,183,910 discloses a sanitary napkin in roll form which is made of detachable interconnected segments. Another patent which broadly teaches this concept is U.S. Pat. No. 2,771,882. A third patent relating to diaper manufacture, i.e., U.S. Pat. No. 1,674,600 also discloses the possibility of producing a hygenic product in roll form. These three patents differ from the subject invention, however, in the fact that in each instance, the napkins or diaper is overlayed by a fluid permeable wrap which surrounds the other components. While the prior art enables the segmentation of individually predetermined length appliances from a prepackaged roll, there is no possibility for bearing either the length or the overall configuration by means of individually shaping the particular sanitary appliance.

DETAILED DESCRIPTION OF THE INVENTION

Figure 1:
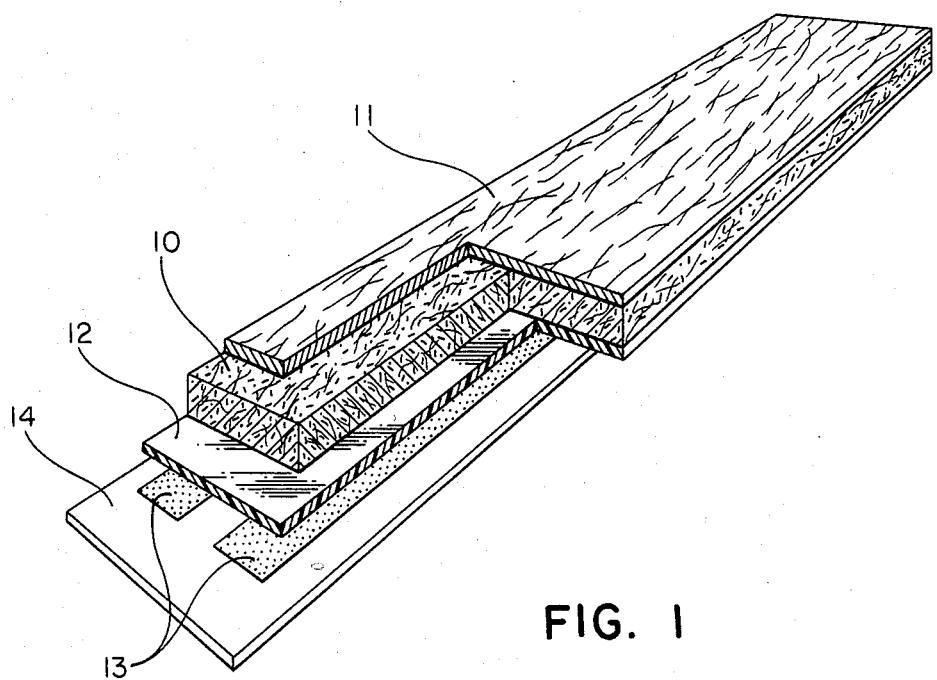
Figure 2:
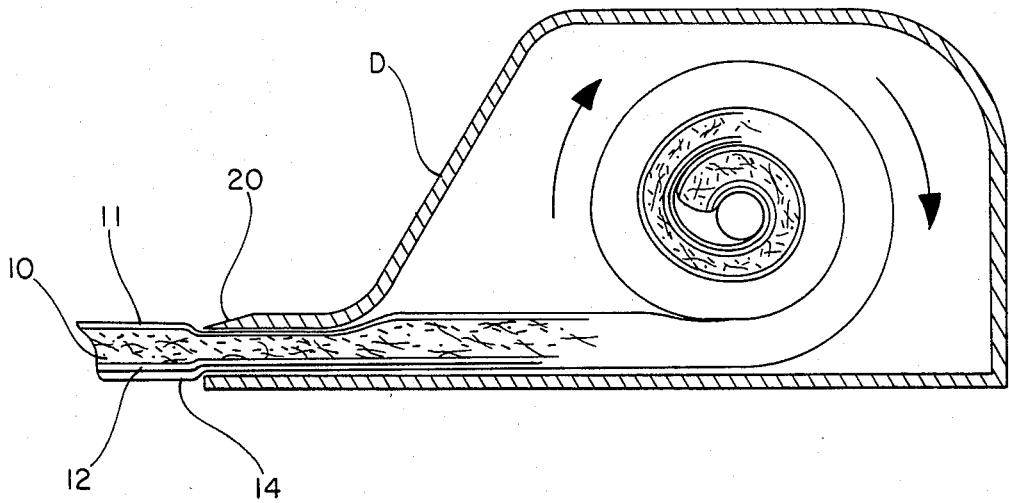

The invention may more readily be understood by reference to the drawings in which FIG. 1 is an exaggerated perspective side view of a segment of the sanitary napkin of this invention and FIG. 2 is a cross-sectional view of the roll of napkin material and suitable dispenser.

As can be seen from the drawings, an absorbent layer 10 is overwrapped with a fluid permeable cover 11. On the opposing side of the absorbent, a fluid impermeable baffle 12 is attached along with a continuous line of adhesive 13 and release liner 14. The baffle (12), the absorbent layer 10, and the cover 11 are held together by conventional means such as adhesive well known in the art. With regard to adhesive configurations, it is desirable that there be at least 2 lines of adhesive disposed longitudinally and extending the length of the entire napkin segment. Obviously the release liner should extend at least as long as the adhesive lines and may desirably extend slightly longer at either end.

As can be seen from FIG. 2 the napkin can be rolled and mounted in a dispenser D. The dispenser may optionally have a cutting edge 20 for longitudinal segmentation although this is not necessary.

While it is preferable that the napkin is wound in a roll it is not necessary that the dispenser shown in FIG. 2 be utilized. The roll can be placed on any spindle and the napkin can be unwound as needed and cut longitudinally by scissors or the like when a segment is desired. This segment may then be cut and shaped as the user requires.

The overall length of the segment prior to rolling should be ample to provide at least one day's napkin wear for a user so that she may conveniently carry a roll of napkins in her purse. Such a roll could be at least 24 inches in length which would provide the average user with 4 or 5 mini pad size napkins. The mini pad size indicated in the preceding sentence is that conventionally used in the pre-formed napkin market.) A purse package is only one possible embodiment. Obviously a sufficient length of napkin segment can be wound in a roll to provide sanitary napkins for at least one and possibly several menstrual cycles. It is envisioned that these napkins would be sold in rolls of various sizes for use with one or several decorative dispensers also of various sizes.

With regard to construction of the napkin segment itself, the cover and fluid impervious baffle can be of any conventional material currently used or contemplated in the art and the particular choice of material for the cover and baffle are not considered part of the present invention for that reason.

It is preferred that the absorbent contain thermoplastic fibers so that the action of cutting either for shaping purposes or for segmenting will serve to provide a partial seal at the cut surfaces. The cutting may in fact be desirably accomplished by a heated blade to further enhance the seal. While the inclusion of themoplastic and the additional bonding is not thought to be critical due to the ability to shape the napkin according to individual configurations it can provide an extra margin of safety. The absorbent component may consist of a single layer of material or multiple layers. A particularly preferred absorbent material is that described in U.S. Pat. No. 4,100,324 which relates to the turbulent intermingling of air formed pulp and thermoplastic microfibers. This material has desirable strength, flexibility and absorbent characteristics when used in this particular product configuration. If the material is a single layer it is preferably in the range of 300-600 grams per square yard basis weight, but if multiple layers are used they may be of varying density and pore size to control the transport and distribution of fluid in the napkin. The theory of capillary attraction and fluid conduction as a result is well known. Also fluid distribution by line embossment of the absorbent layer or layers can be beneficial in providing maximum utilization without leakage for the napkin formed from the napkin roll of this invention.

A measure of absorbent integrity is the dry and wet Cohesion Test developed by Kimberly-Clark Corporation. This test consists of mounting a napkin or absorbent layer between two platens and adhesively attaching each side. A steady force is applied to one platen while the other remains stationary. The rate of travel of the moveable paten is 30.5 cm/min. A force gauge attached to the moveable platen measures the amount of force needed to rupture the absorbent. A comparative test which measures wet cohesion is performed by the same method except that 3.0 cc's water is added slowly to the pad near the center and the pad is held for 1 minute after water addition.

For napkins of this invention cohesion values of 0.8 kg dry and 0.5 kg wet provide realistic minimum values for integrity in the, i.e., vertical direction of the absorbent.

What is claimed is:

1. A sanitary napkin comprising a flexible elongated length of material comprising a fluid pervious cover, an absorbent matrix and a fluid impervious baffle, at least two longitudinal lines of attachment adhesive on said baffle, each of said baffle, said adhesive lines, cover and absorbent being substantially coterminous at their longitudinal edges and being at least 24 inches in length, said elongated length of material being devoid of predetermined detachable segments, said absorbent further defined by a dry cohesion value of not less than 0.8 Kg and a wet cohesion value of not less than 0.5 Kg.

2. A wound roll of composite material in combination with a dispenser for said roll, said dispenser having means for rotatably mounting said roll and said composite material being a sanitary napkin comprising a flexible elongated length of material comprising a fluid pervious cover, an absorbent matrix and a fluid impervious baffle, at least two longitudinal lines of attached adhesive on said baffle, each of said baffle, said adhesive lines, cover and absorbent being substantially coterminous at their longitudinal edges and being at least 24 inches in length, said elongated length of material being devoid of predetermined detachable segments, said absorbent further defined by a dry cohesion value of not less than 0.8 Kg and a wet cohesion value of not less than 0.5 Kg.

3. A combination of claim 2 wherein the dispenser is provided with a cutting edge.

4. The product of claims 1, 2, or 3 wherein the absorbent layer contains thermoplastic material.

5. The product of claims 1, 2, or 3 wherein the absorbent material is a coformed air-laid turbulently intermingled mixture of pulp and thermoplastic microfibers.

6. The product of claims 1, 2, or 3 wherein the absorbent material has a basis weight of 300-600 grams per square yard.

* * * * *